United States Patent [19]

Soula

[11] Patent Number: 4,560,814

[45] Date of Patent: Dec. 24, 1985

[54] PROCESS FOR ALKYLATING HALOGENATED AND TRIFLUOROMETHYLATED BENZENE COMPOUNDS

[75] Inventor: Gerard Soula, Meyzieu, France

[73] Assignee: Rhone-Poulenc Specialites Chimiques, Courbevoie, France

[21] Appl. No.: 575,586

[22] Filed: Jan. 31, 1984

[30] Foreign Application Priority Data

Feb. 2, 1983 [FR] France ............................... 83 01594

[51] Int. Cl.$^4$ .............................................. C07C 17/26
[52] U.S. Cl. ................................... 570/144; 570/190; 570/191
[58] Field of Search ................ 570/144, 191, 143, 190

[56] References Cited

U.S. PATENT DOCUMENTS 3,297,771  1/1967  Lebrick et al. ...................... 260/651
4,059,642  11/1977 Dewald et al. ..................... 570/190

FOREIGN PATENT DOCUMENTS 2026481  9/1970  France .
2052947  4/1971  France .
2450120  9/1980  France .
 794153  4/1958  United Kingdom .

Primary Examiner—Charles F. Warren
Assistant Examiner—Joseph A. Boska

[57] ABSTRACT

Disclosed is a process for alkylating halogenated and trifluoromethylated benzene compounds. In that process, an alkyl halide is reacted with a benzene compound having two or three substituents selected from the group consisting of the halogens and the trifluoromethyl group, and also having a hydrogen atom whose two ortho positions are occupied by two of the said substituents. The reaction is carried out in the presence of at least one alkali metal amide and at least one agent that complexes with the cation of the alkali metal amide.

20 Claims, No Drawings

PROCESS FOR ALKYLATING HALOGENATED AND TRIFLUOROMETHYLATED BENZENE COMPOUNDS

FIELD OF THE INVENTION

The present invention relates to an improved process for alkylating halogenated and trifluoromethylated benzene compounds by reacting those compounds with an alkyl halide. More particularly, the present invention is directed to a process for alkylating dihalobenzenes, trihalobenzenes, and the corresponding benzene compounds wherein one or more of the halogen atoms is replaced by a trifluoromethyl group, in which the benzene compounds have at least one hydrogen atom whose two ortho positions are occupied by halogen atoms, trifluoromethyl groups, or a halogen atom and a trifluoromethyl group. The alkylated benzene compounds produced by the process of the present invention are useful as herbicides. In addition, alkylated dichlorobenzene compounds made by the process of the invention may be used in a known manner as intermediates in the production of the herbicide 2,6-dichlorobenzonitrile. In turn, 2,6-dichlorobenzonitrile may be used, again in a known manner, to make the herbicide chlorothiamide.

BACKGROUND OF THE INVENTION

It is known that halogenated benzene compounds may be alkylated by the Friedel-Crafts reaction by acid catalysis (MARCH, Advanced Organic Chemistry, 1977). The known method favors alkylation of the benzene compounds at the para position. For example, alkylation of metadichlorobenzene by the known method produces predominantly 2,4-dichloroalkylbenzene, with a lesser amount of 2,6-dichloroalkylbenzene being produced. In addition, during acid catalysis, the alkyl chain of the alkylating agent tends to be rearranged when the chain is sufficiently long to permit such rearrangement. For example, when n-butyl bromide is used as the alkylating agent, an isobutyl group rather than an n-butyl group is attached to the benzene ring.

One consequence of the limitations of the prior art process discussed above is that it is not possible by that process to produce from a dihalobenzene, which has a hydrogen atom whose two ortho positions are occupied by halogens, major quantities of an alkylated benzene product in which the alkyl group is positioned in the ortho position with respect to the two halogen groups. In addition, it is not possible to produce major quantities of certain alkylated benzene products by that process because of the rearrangement of certain alkyl groups described above.

SUMMARY OF THE INVENTION

The present invention is directed to a process for alkylating halogenated and trifluoromethylated benzene compounds which does not suffer from the limitations of the prior art process described above. In contrast to that prior art process, the process of the present invention is carried out in a basic medium comprising an alkali metal amide and a complexing agent for the cation of the alkali metal amide.

More particularly, the process of the present invention comprises reacting: (a) a benzene compound having two or three substituents selected from the group consisting of the halogens and the trifluoromethyl group, and also having a hydrogen atom whose two ortho positions are occupied by two of the said substituents with (b) an alkyl halide to produce an alkylated benzene derivative. The foregoing reaction is carried out in the presence of at least one alkali metal amide and at least one agent that forms a complex with the cation of the alkali metal amide.

DESCRIPTION OF THE PREFERRED EMBODIMENTS

The benzene compounds that are used as reactants in preferred processes of the invention have the formula:

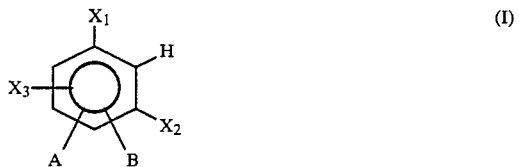

wherein $X_1$ and $X_2$ are, simultaneously or independently, halogen or a trifluoromethyl group, $X_3$ is —H, halogen, or a trifluoromethyl group or alkyl group having 1 to 6 carbon atoms, and A and B are, independently or simultaneously, —H or an alkyl group having 1 to 6 carbon atoms.

Examples of compounds of formula I that may be used in the process of the present invention are metadichlorobenzene, metadifluorobenzene, metafluorochlorobenzene, metafluorobromobenzene, metachlorobromobenzene, metadibromobenzene, 1,3,5-trichlorobenzene, 1,2,4-trichlorobenzene, 3,5-dichlorofluorobenzene, 2,4-dichlorotoluene, 1,3-chlorotrifluoromethylbenzene, and 1,3-ditrifluoromethylbenzene.

The alkyl halide reactant that is used in preferred processes of the invention has the formula:

$$R(X_4)_n \qquad (II)$$

wherein $X_4$ is halogen, R is an alkyl group having 1 to 12 carbon atoms, and n is equal to 1 or 2.

Some examples of compounds of formula (II) that may be used in the process of the present invention are the methyl, ethyl, propyl, and butyl halides and their higher homologs.

As previously mentioned, the reaction of the process of the invention is carried out in the presence of an alkali metal amide. Preferred amides are the sodium, potassium, and lithium amides. Sodium amide is most preferred.

An agent for complexing with the cation of the alkali metal amide is also included in the reaction mixture. One class of preferred complexing agents that may be used is the macrocyclic polyethers which are known in the art as "crown ethers" and which are described in French Pat. No. 2,026,481. Such "crown ethers" have 15 to 30 atoms in their respective rings and include 5 to 10 —O—X— units wherein X is —CHR$_1$—CHR$_2$— or —CHR$_1$—CHR$_4$—CR$_3$R$_2$—, and R$_1$, R$_2$, R$_3$, and R$_4$ are, independently or simultaneously, —H or an alkyl group having 1 to 4 carbon atoms, and further wherein one of the —O—X— units may be —O—CHR$_1$—CHR$_4$—CR$_3$R$_2$— when the remainder of the —O—X— units are —O—CHR$_1$—CHR$_2$—.

Examples of the crown ethers that may be used in the process of the invention are:

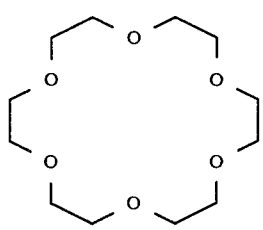

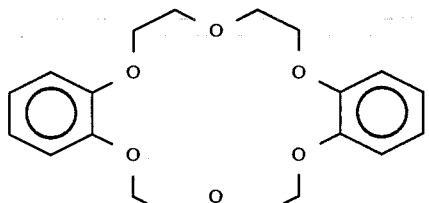

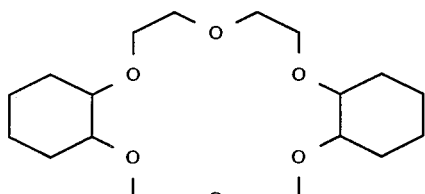

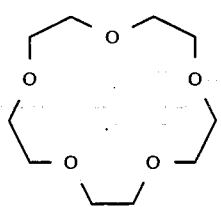

Another class of preferred complexing agents that may be used in the process of the present invention are the compounds having formulas IIIa and IIIb below:

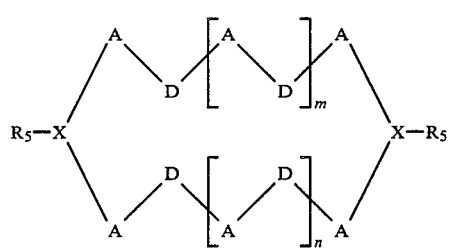
(IIIa)

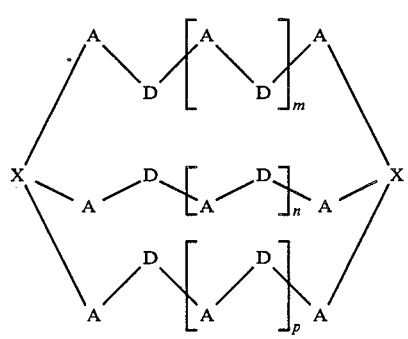
(IIIb)

wherein X is —N or —P, A is an alkylene group having 1 to 3 carbon atoms, D is —O, —S, or —NR$_6$ where R$_6$ is an alkyl group having 1 to 6 carbon atoms, R$_5$ is an alkyl group having 1 to 6 carbon atoms, and n, m, and p are, simultaneously or independently, integers from 0 to 5.

Compounds of the formulas IIIa and IIIb are described in French Pat. No. 2,052,947. The following are examples of such compounds that are suitable for use in the process of the invention:

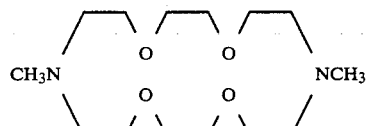

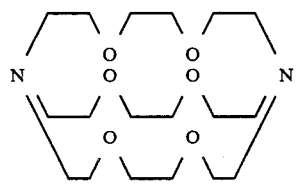

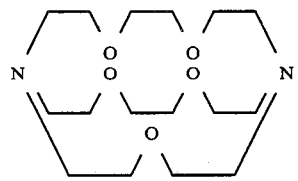

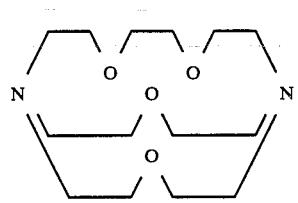

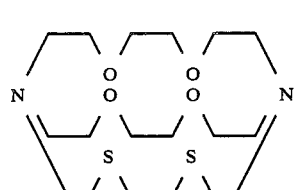

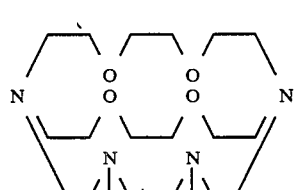

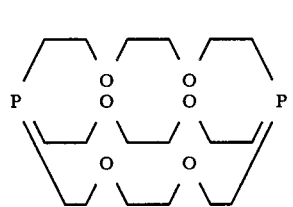

Yet another class of preferred complexing agents that may be used in the process of the invention are amines of the formula:

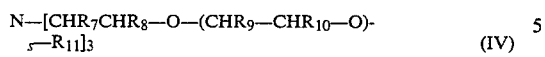
$$N-[CHR_7CHR_8-O-(CHR_9-CHR_{10}-O)_s-R_{11}]_3 \quad (IV)$$

wherein s is an integer from 0 to 10, (0≦s≦10), $R_7$, $R_8$, $R_9$, and $R_{10}$ are, independently or simultaneously, —H or an alkyl group having 1 to 4 carbon atoms, and $R_{11}$ is an alkyl group having 1 to 12 carbon atoms, a cycloalkyl group having 1 to 12 carbon atoms, phenyl ($\phi$), —$C_qH_{2q}$—$\phi$ or $C_qH_{2q+1}$—$\phi$—, where q is an integer from 1 to 12.

The amines of formula IV above are described in French Pat. No. 2,450,120.

The preferred amines of formula IV are those in which $R_7$, $R_8$, $R_9$, and $R_{10}$ are —H or methyl. More preferred are those amines in which s is an integer from 0 to 6 and $R_{11}$ is an alkyl group having 1 to 4 carbon atoms.

The following amines can be used as the complexing agent in the process of the invention:
tris(3-oxaheptyl)amine [N—(CH₂—CH₂—O—C₄H₉)₃];
tris(3,6-dioxaheptyl)amine [N—(CH₂—CH₂—O—CH₂—CH₂—O—CH₃)₃]; tris(3,6,9-trioxadecyl)amine [N—(CH₂—CH₂—O—CH₂—CH₂—O—CH₂—CH₂O—CH₃)₃]; tris(3,6-dioxaoctyl)amine [N—(CH₂—CH₂—O—CH₂—CH₂—O—C₂H₅)₃]; tris(3,6,9-trioxaundecyl)amine [N—(CH₂—CH₂—O—CH₂—CH₂—O—CH₂—CH₂—O—C₂H₅)₃]; tris(3,6-dioxanonyl)amine [N—(CH₂—CH₂—O—CH₂—CH₂—O—C₃H₇)₃]; tris(3,6,9-trioxadodecy)amine [N—(CH₂—CH₂—O—CH₂—CH₂—O—CH₂—CH—O—C₃H₇)₃]; tris(3,6-dioxadecyl)amine [N—(CH₂—CH₂—O—CH₂—CH₂—O—C₄H₉)₃]; tris(3,6,9-trioxatridecyl)amine [N—(CH₂—CH₂O—CH₂—CH₂—O—CH₂—CH₂—O—C₄H₉)₃]; tris(3,6-dioxa-4-methylheptyl)amine [N—(CH₂—CH₂—O—CHCH₃—CH₂—O—CH₃)₃]; and tris(3,6-dioxa-2,4-dimethylheptyl)amine [N—(CH₂—CHCH₃—O—CH—CH₂—O—CH₃)₃].

Another class of complexing agents that may be used in the process of the present invention are linear polyethers of the formula:

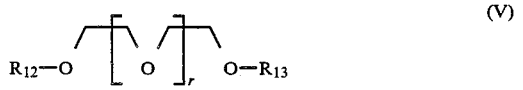
(V)

wherein r is an integer, preferably from 1 to 10, and $R_{12}$ and $R_{13}$, which may be the same or different, are an alkyl group having 1 to 12 carbon atoms.

More preferred are polyethers of formula V in which r is an integer from 1 to 4, and in which $R_{12}$ is an alkyl group having 1 to 6 carbon atoms.

The following are examples of compounds of formula (V) that may be used in the process of the present invention:

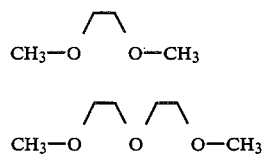

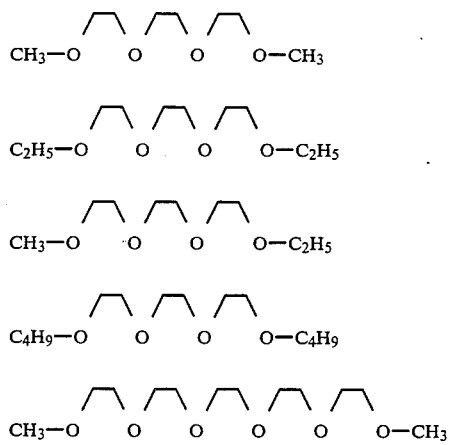

Each of the complexing agents specified above may be used alone as the sole complexing agent. Alternatively, mixtures of the complexing agents described above may be used.

Monoalkylation, dialkylation, or both may occur during the process of the present invention. Because it is preferred to use a slight stoichiometric excess of alkyl halide, the preferred molar ratio of the alkyl halide to the benzene compound added to the reaction mixture is slightly greater than 1 in those cases where only monoalkylation occurs. In those cases where dialkylation occurs, the preferred molar ratio is greater than 2.

The preferred molar ratio of the alkali metal amide to the benzene compound added to the reaction mixture is at least 1. More preferably, the ratio is between 1 and 3.

The preferred molar ratio of the complexing agent to the benzene compound added to the reaction mixture is 0.01 to 0.2. More preferably, the ratio is 0.03 to 0.1.

The reaction may be carried out in the presence or absence of a solvent. However, if a solvent is used, it should be inert under the reaction conditions. Such inert solvents include toluene, tetrahydrofuran, dioxane, benzene and ethyl ether.

The preferred reaction temperature is between −40° C. and 100° C. A reaction temperature between −10° C. and 60° C. is most preferred.

The process of the invention may be carried out at atmospheric pressure as well as at pressures above or below atmospheric pressure.

It is believed that the alkali metal amide functions to remove the hydrogen situated between the $X_1$ and $X_2$ substitutents of the commpound of formula I. This gives rise to the following compound:

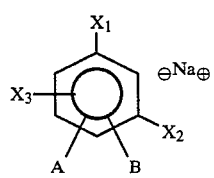

The cation of the above compound is complexed with the complexing agent to solubilize the compound in the reaction medium. This, in turn, enables the above compound to react with the alkyl halide to obtain the reaction product:

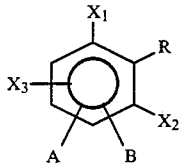
(VI)

The specificity of the reaction of the process of the present invention is particularly advantageous in certain cases. For example, the process provides a means to obtain a valuable product from the residual mixture obtained during the manufacture of orthodichlorobenzene. That residual mixture comprises a mixture of metadichlorobenzene and paradichlorobenzene that is difficult to separate by conventional techniques such as fractional distillation or crystallization. Consequently, the metadichlorobenzene contained in the mixture typically is lost. The process of the instant invention, however, now makes it possible to recover the metadichlorobenzene by reacting it with a methyl halide to produce 2,6-dichlorotoluene, a valuable product which may be separated from the paradichlorobenzene which did not react with the methylhalide.

The following examples present illustrative, but non-limiting, embodiments of the present invention.

EXAMPLE 1

This example illustrates the alkylation of 1,3,5-trichlorobenzene by n-bromobutane.

7.8 g of a 50% suspension of sodium amide in toluene were added, under nitrogen, to a 200 ml reactor equipped with a magnetic stirrer, a dropping funnel, and a reflux condenser, the condenser being followed by a tube immersed in an aqueous solution of hydrochloric acid. The mixture was cooled to 5° C. over the course of 15 minutes. A solution containing 9.1 g (0.05 mole) of 1,3,5-trichlorobenzene, 1.6 g (0.005 mole) of tris(3,6-dioxaheptyl)amine, and 40 g of toluene was then added to the reactor.

Over the course of 1 hour, 13.7 g (0.1 mole) of 1-bromobutane were added to the reactor while the reaction medium was agitated and maintained at a temperature of 17° C. Following the addition of 100 ml of water and separation of the organic phase, the latter was analyzed by gas chromatography. Nearly complete disappearance of the 1,3,5-trichlorobenzene (conversion=98%) was noted with the formation of a monoalkylated product (selectivity=73%); and a dialkylated product (selectivity=27%).

EXAMPLE 2

This example illustrates the alkylation of 1,3-dichlorobenzene by bromoethane.

6 g of a 50% suspension of sodium amide in toluene were added, under nitrogen, to a 200 ml reactor equipped as in Example 1. The mixture was cooled to 5° C. 7.35 g (0.05 mole) of 1,3-dichlorobenzene, and 0.8 g (0.0025 mole) of tris(3,6-dioxaheptyl)amine dissolved in 20 g of toluene were then added to the reactor. Then, over the course of 1 hour, 8.17 g (0.075 mole) of bromoethane were added while the temperature of the reaction medium was maintained at 18° C. The reaction was continued for 5 hours before 100 ml of water were added to stop the reaction and to dissolve all the inorganic salts present in the mixture. The organic phase was recovered and dried. Analysis by gas chromatography showed the production of a monoalkylated product (1-ethyl-2,6-dichlorobenzene), with a conversion of 80% and a selectivity of 94%.

EXAMPLE 3

This example illustrates the alkylation of 1-fluoro-3-chlorobenzene by methyl chloride.

8.3 g of a 50% suspension of sodium amide in toluene were added, under nitrogen, to a 200 ml reactor equipped as in Example 1. After cooling to 10° C., there were added 13 g (0.1 mole) of 1-chloro-3-fluorobenzene and 1.6 g (0.005 mole) of tris(3,6-dioxaheptyl)amine in 20 g of dimethoxyethane. Next, gaseous methyl chloride was added to the reactor while the reaction medium was agitated and its temperature maintained at 18° C. The reaction was continued for 5 hours before 100 ml of water were added to stop the reaction and to dissolve the inorganic salts present in the mixture. The organic phase was decanted, separated, and dried using silica gel. The toluene was removed under reduced pressure and the crude mixture distilled. 7.3 g of unconverted metachlorofluorobenzene and 6 g of 2-chloro-6-fluorotoluene (bp=145°–150° C. at 760 mm Hg) were recovered.

EXAMPLE 4

This example illustrates the alkylation of 1-chloro-3-trifluoromethylbenzene by methyl chloride.

5.85 g of a 50% suspension of sodium amide in toluene were added, under nitrogen, to a 200 ml reactor equipped as in Example 3. After cooling to 16° C., 9.07 g (0.05 mole) of 1-chloro-3-trifluoromethylbenzene and 0.8 g (0.0025 mole) of tris(3,6-dioxaheptyl)amine in 15 g of dimethoxyethane were added. Next, gaseous methyl chloride was added to the reactor while the reaction medium was agitated and its temperature maintained at about 23° C. The reaction was continued for 6 hours before 20 ml of water were added to stop the reaction and to dissolve the inorganic salts formed in the mixture.

Analysis by gas chromatography showed the production of 6-trifluoromethyl-1-chlorotoluene, with a conversion of 37% and a selectivity of 90%.

EXAMPLE 5

This example illustrates the alkylation of 1,3-ditrifluoromethylbenzene by methyl chloride.

5.85 g of a 50% suspension of sodium amide in toluene were added, under nitrogen, to a 200 ml reactor equipped as in Example 3. After cooling to 15° C., 10.7 g (0.05 mole) of 1,3-ditrifluoromethylbenzene and 0.8 g (0.0025 mole) of tris(3,6-dioxaheptyl)amine in 15 g of dimethoxyethane were added. Next, gaseous methyl chloride was added to the reactor while the reaction medium was agitated and its temperature maintained at about 20° C. The reaction was continued for 4 hours before 20 ml of water were added to stop the reaction and to dissolve the inorganic salts formed in the mixture.

Analysis by gas chromatography showed the production of 2,6-ditrifluoromethyltoluene with a conversion of 16% and a selectivity of 86%.

EXAMPLE 6

This example illustrates the alkylation of 2,4-dichlorotoluene by methyl chloride.

5.85 g of a 50% suspension of sodium amide in toluene were added, under nitrogen, to a 200 ml reactor equipped as in Example 3. After cooling to 16° C., 8.05 g (0.05 mole) of 2,4-dichlorotoluene and 0.8 g (0.0025 mole) of tris(3,6-dioxaheptyl)amine in 15 g of dimethoxyethane were added. Next, gaseous methyl chloride was added to the reactor while the reaction medium was agitated and its temperature maintained at about 23° C. The reaction was continued for 7 hours before 20 ml of water were added to stop the reaction and to dissolve the inorganic salts formed in the mixture.

Analysis by gas chromatography showed the production of 3-methyl-2,4-dichlorotoluene with a conversion of 27% and a selectivity of 95%.

EXAMPLE 7

This example illustrates the alkylation of 1,3-dichlorobenzene by methyl chloride.

5.85 g of a 50% suspension of sodium amide in toluene were added, under argon, to a 200 ml reactor equipped as in Example 3. After cooling to 17° C., 7.35 g (0.05 mole) of 1,3-dichlorobenzene and 0.94 g (0.0025 mole) of "kriptofix 222" (1,7,10,16-tetraoxa-4,13-diazacyclooctadecane) in 15 g of toluene were added over the course of 10 minutes. Next, gaseous methyl chloride was added to the reactor while the reaction medium was stirred and its temperature maintained at approximately 21° C. The reaction was continued for 18 hours before 20 ml of water were added to stop the reaction and to dissolve the inorganic salts formed in the mixture.

Analysis by gas chromatography showed a conversion of 60% with the production of a monoalkylation product (2,6-dichlorotoluene, selectivity=70%), and a dialkylation product (2,6-dichloroethylbenzene, selectivity=30%).

EXAMPLE 8

This example illustrates the alkylation of 1,3-dichlorobenzene by methyl chloride.

5.85 g of a 50% suspension of sodium amide in toluene were added, under argon, to a 200 ml reactor equipped as in Example 3. After cooling to 17° C., 7.35 g (0.05 mole) of 1,3-dichlorobenzene and 0.7 g of dicyclohexyl-18-crown-6 (molecular weight, 372 g) in 15 g of tetrahydrofurane were added over a period of 5 minutes. Next, gaseous methyl chloride was added to the reactor while the reaction medium was stirred and its temperature maintained at 23° C. The reaction was continued for 23 hours before 20 ml of water were added to stop the reaction and to dissolve the inorganic salts formed in the mixture.

Analysis by gas chromatography showed the production of 2,6-dichlorotoluene with a conversion of 40% and a selectivity of 96%.

EXAMPLE 9

This example illustrates the alkylation of 1,3-dichlorobenzene by methyl chloride.

5.85 g of a 50% suspension of sodium amide in toluene were added, under argon, to a 200 ml reactor equipped as in Example 3. Over the course of 3 minutes, 7.35 g (0.05 mole) of 1,3-dichlorobenzene and 1 g (0.00025 mole) of polyethylene glycol 400 (dimethyl ether of polyethylene glycol) in 15 g of tetrahydrofuran were added. Next, gaseous methyl chloride was added to the reactor while the reaction medium was stirred and its temperature maintained at 22° C. The reaction was continued for 23 hours before 20 ml of water were added to stop the reaction and to dissolve the inorganic salts formed in the mixture. After recovery of the unconverted 1,3-dichlorobenzene, the product was distilled at reduced pressure (bp=120°-124° C. at 100 mm Hg).

Analysis by gas chromatography showed the production of 2-6-dichlorotoluene, with a conversion of 30% and a selectivity of 94%.

What is claimed is:

1. A process for alkylating halogenated and trifluoromethylated benzene compounds which comprises reacting an alkyl halide with a benzene compound having two or three substituents selected from the group consisting of the halogens and a trifluoromethyl group and also having a hydrogen atom whose two ortho positions are occupied by two of the said substituents, the reaction being carried out in the presence of at least one alkali metal amide and at least one agent that complexes with the cation of the alkali metal amide to produce a reaction product comprising an alkylated benzene derivative.

2. The process of claim 1 wherein the alkyl halide reactant has the formula $R(X_4)_n$ wherein $X_4$ is halogen, R is an alkyl group having 1 to 12 carbon atoms, and n is equal to 1 or 2.

3. The process of claim 1 wherein the agent that complexes with the cation of the alkali metal amide is a macrocyclic polyether having 15 to 30 atoms in its ring which includes 5 to 10 —O—X— units wherein X is —CHR$_1$—CHR$_2$— or —CHR$_1$—CHR$_4$—CR$_3$R$_2$—, and R$_1$, R$_2$, R$_3$ and R$_4$ are, independently or simultaneously, —H or an alkyl group having 1 to 4 carbon atoms, and further wherein one of the —O—X— units may be —O—CHR$_1$—CHR$_4$—CR$_3$R$_2$— when the remainder of the —O—X— units are —O—CHR$_1$—CHR$_2$—.

4. The process of claim 1 wherein the agent that complexes with the cation of the alkali metal amide is a macrocyclic or bicyclic compound of the formula IIIa or IIIb:

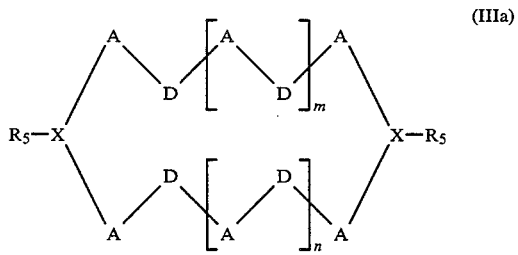

(IIIa)

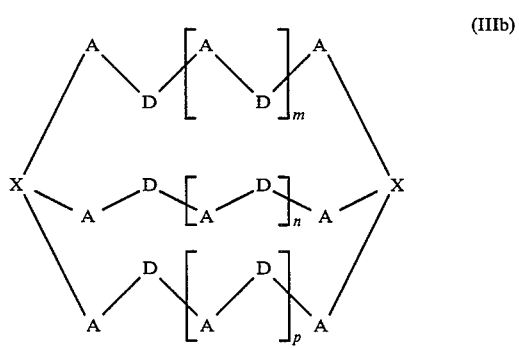

(IIIb)

wherein:

X is —N or —P, A is an alkylene group having 1 to 3 carbon atoms, D is —O, —S, or —N—R$_6$ where $R_6$ is an alkyl radical having 1 to 6 carbon atoms, $R_5$ is an alkyl group having 1 to 6 carbon atoms, and n, m, and p are, simultaneously or independently, integers from 0 to 5.

5. The process of claim 1 wherein the agent that complexes with the cation of the alkali metal amide is an amine of the formula:

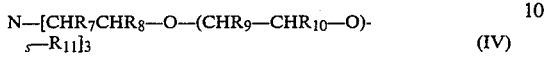
(IV)

wherein s is an integer from 0 to 10 ($0 \leq s \leq 10$), $R_7$, $R_8$, $R_9$, and $R_{10}$ are, independently or simultaneously, —H or an alkyl group having 1 to 4 carbon atoms, and $R_{11}$ is an alkyl group having 1 to 12 carbon atoms, a cycloalkyl group having 1 to 12 carbon atoms, phenyl ($\phi$), —$C_qH_{2q}$—$\phi$, or $C_qH_{2q+1}$—$\phi$—, where q is an integer from 1 to 12.

6. The process of claim 1 wherein the agent that complexes with the cation of the alkali metal amide is a linear polyether of the formula:

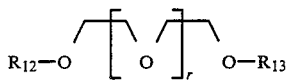
(V)

wherein r is an integer from 1 to 10, and $R_{12}$ and $R_{13}$ are, independently or simultaneously, an alkyl group having 1 to 12 carbon atoms.

7. The process of claim 3 wherein the macrocyclic polyether is selected from the group consisting of:

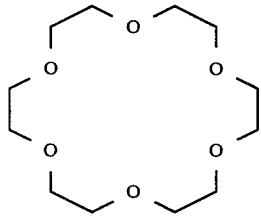

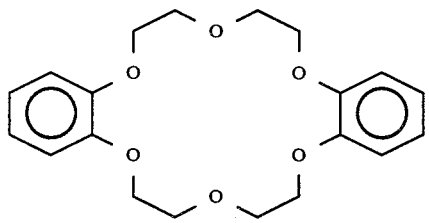

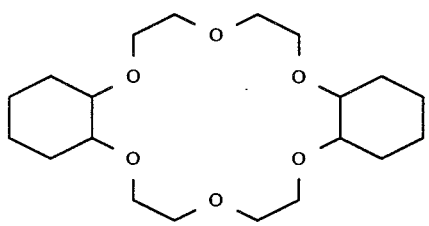

-continued

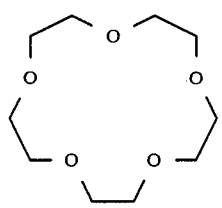

8. The process of claim 4 wherein the macrocyclic or bicyclic compound is selected from the group consisting of:

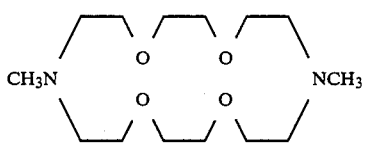

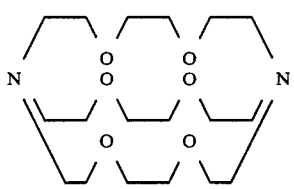

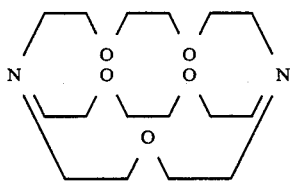

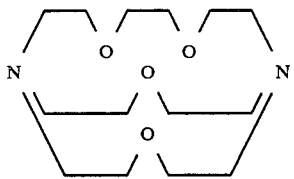

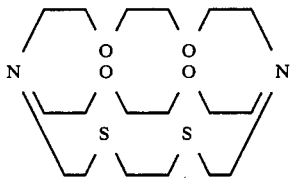

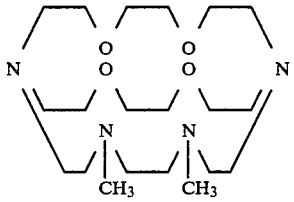

-continued

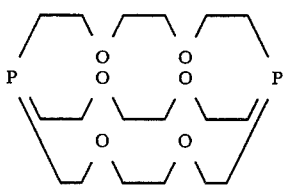

9. The process of claim 5 wherein $R_7$, $R_8$, $R_9$, and $R_{10}$ are, simultaneously or independently, —H or a methyl group.

10. The process of claim 5 wherein s is an integer from 0 to 6, and $R_{11}$ is an alkyl group having 1 to 4 carbon atoms.

11. The process of claim 5 wherein the amine is tris(3,6-dioxaheptyl)amine or tris(3,6-dioxaoctyl)amine.

12. The process of claim 6 wherein the linear polyether is selected from the group consisting of:

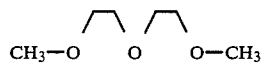

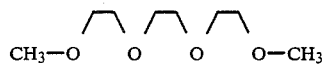

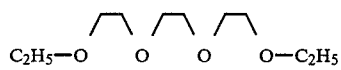

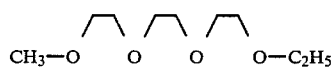

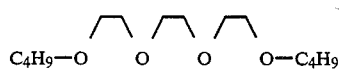

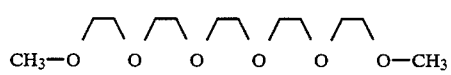

13. The process of claim 1 wherein the alkali metal amide is sodium, potassium, or lithium amide.

14. The process of claim 1 wherein the molar ratio of the alkali metal amide to the benzene compound is at least 1.

15. The process of claim 1 wherein the molar ratio of the agent that complexes with the cation of the alkali metal amide to the benzene compound is 0.01 to 0.2.

16. The process of claim 1 wherein a slight stoichiometric excess of alkyl halide is used.

17. The process of claim 1 wherein the reaction is carried out at a temperature between —40° C. and +100° C.

18. A process for alkylating halogenated and trifluoromethylated benzene compounds which comprises reacting an alkyl halide with a benzene compound having the formula:

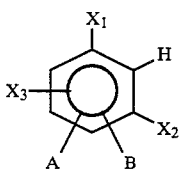

wherein $X_1$ and $X_2$ are, simultaneously or independently, halogen or a trifluoromethyl group, $X_3$ is —H, halogen, a trifluoromethyl group or an alkyl group having 1 to 6 carbon atoms, and A and B are, simultaneously or independently, —H or an alkyl group having 1 to 6 carbon atoms, the reaction being carried out in the presence of at least one alkali metal amide and at least one agent that complexes with the cation of the alkali metal amide to produce a reaction product comprising an alkylated benzene derivative.

19. The process of claim 18 wherein the alkyl halide reactant has the formula $R(X_4)_n$ wherein $X_4$ is halogen, R is an alkyl group having 1 to 12 carbon atoms, and n is equal to 1 or 2.

20. The process of claim 19 wherein the alkali metal amide is sodium, potassium, or lithium amide.

* * * * *